United States Patent [19]

Weller et al.

[11] Patent Number: 4,647,533

[45] Date of Patent: Mar. 3, 1987

[54] METHOD FOR SCREENING BACTERIA AND APPLICATION THEREOF FOR FIELD CONTROL OF PYTHIUM SPP. ON SMALL GRAIN CROPS

[75] Inventors: David M. Weller; R. James Cook, both of Pullman, Wash.; J. Ole Becker, Gent, Belgium

[73] Assignee: The United States of America as represented by the Secretary of Agriculture, Washington, D.C.

[21] Appl. No.: 650,739

[22] Filed: Sep. 14, 1984

[51] Int. Cl.$^4$ .......................... C12Q 1/02; C12Q 1/24; C12R 1/39; C12R 1/40

[52] U.S. Cl. .......................................... 435/29; 47/58; 71/3; 71/6; 435/30; 435/34; 435/876; 435/877

[58] Field of Search ..................... 435/29, 30, 34, 876, 435/877; 47/58; 71/3, 6

[56] References Cited

U.S. PATENT DOCUMENTS 4,456,684  6/1984  Weller et al. .......................... 435/34

OTHER PUBLICATIONS

Suslow, *Phytopathogenic Prokaryotes*, vol. I, pp. 187–223, (1982).
Schroth et al., *Ann. Rev. Microbiol.*, 35; pp. 453–476, (1981).
Baker, *Ann. Rev. of Phytopathology*, 6, pp. 263–294, (1968).
Burr et al., *CRC Critical Reviews in Plant Sciences*, vol. 2, Issue 1, pp. 1–20.
U.S. Ser. No. 500,043, R. D. Lumsen et al., 6/1/1983.
R. James Cook and W. A. Haglund, Pythium Root Rot: A Barrier to Yield of Pacific Northwest Wheat, Research Bulletin XB 0913, Agricultural Research Center, Washington State University, (1982).
Price, R. D., K. F. Baker, P. Broadbent, and E. H. Ridge, 1971, Effect on Wheat Plants of a Soil or Seed Application of *Bacillus subtilis*, either with or without the Presence of *Rhizoctonia solani*, Proc. Aust. Conf. Soil Biology, pp. 50–51, (Reprint not available, description taken from *Biological Control of Plant Pathogens* by K. F. Baker and R. J. Cook, The American Phytopathological Society, St. Paul, MN p. 92, (1982).
P. Broadbent, K. F. Baker and Y. Waterworth, "Bacteria and Actinomycetes Antagonistic to Fungal Root Pathogens in Australian Soils", *Aust. J. Biol. Sci.*, vol. 24, pp. 925–944, (1971).
P. R. Merriman, R. D. Price and K. F. Baker, "The Effect of Inoculation of Seed with Antagonists of *Rhizoctonia solani* on the Growth of Wheat", *Aust. J. Agric. Research*, vol. 25, pp. 213–218, (1974).
P. R. Merriman, R. D. Price, J. F. Kollmorgen, T. Piggott and E. H. Ridge, "Effect of Seed Inoculation with *Bactillus subtilis* and *Streptomyces griseus* on the Growth of Cereals and Carrots, *Aust. J. Agric Res.*, vol. 25, pp. 219–226, (1974).
M. N. Schroth and J. G. Hancock, "Disease-Suppressive Soil and Root-Colonizing Bacteria", *Science*, vol. 216, pp. 1376–1381, (1982).
C. R. Howell and R. D. Stipanovic, "Control of *Rhizoctonia solani* on Cotton Seedlings with *Pseudomonas fluorescens* and with an Antibiotic Produced by the Bacterium, *Phytopathology*, vol. 69, No. 5, pp. 480–482, (1979).
C. R. Howell and R. D. Stipanovic, "Suppression of *Pythium ultimum*-Induced Damping-Off of Cotton Seedlings by *Pseudomonas fluorescens* and its Antibiotic, Pyoluteorin, *Phytopathology*, vol. 70, No. 8, pp. 712–715, (1980).

*Primary Examiner*—Sidney Marantz
*Assistant Examiner*—Patricia Kate White
*Attorney, Agent, or Firm*—M. Howard Silverstein; David G. McConnell; Margaret A. Connor

[57] ABSTRACT

A method for screening bacteria to select strains which will suppress Pythium spp. in small grain crops under field conditions and a method for applying field-suppressive bacteria to suppress Pythium spp. in a commercial setting are described. Four Pseudomonas strains which passed the screen test are disclosed.

15 Claims, No Drawings

METHOD FOR SCREENING BACTERIA AND APPLICATION THEREOF FOR FIELD CONTROL OF PYTHIUM SPP. ON SMALL GRAIN CROPS

BACKGROUND OF THE INVENTION

This invention relates to novel strains of bacteria which have the ability to control Pythium spp. on small grains under field conditions and a method for the selection of these strains.

The soilborne pathogen complex of Pythium spp. comprises a group of fungi that are among the most successful of all microbial colonists in agricultural soils. It is estimated that nearly all cultivated soil in the world contains spores of at least one, two, three, and even as high as ten Pythium species. The normal nutritional substrate of this pathogen complex are roots of agricultural crops and it is known to cause serious damage to small grain crops such as wheat, oats, barley, rye, and triticale. Such damage includes seed decay, preemergence seedling blight, damage to fine rootlets and root hairs, reduced root length, plant stunting, reduced tillering, uneven height, delayed maturity, and reduced yield. At least ten species of Pythium are known to adversely effect wheat production in the Pacific Northwest (Washington, Oregon, and Idaho), and it has been estimated that Pythium damage causes reduction in wheat yields in this area of 10 to 25 percent, resulting in significant economic losses. This problem may worsen as growers move to minimum and no-till practices. Although exact losses of small grain crops due to Pythium on a worldwide basis are not known, Pythium root rot is considered a serious root disease which causes significant reduction in crop yields.

Presently, the only completely effective method to control Pythium spp. is by soil fumigation using fungicides such as Telone C (1,3-dichloropropene plus 15-17% chloropicrin) or CP 440 (chloropicrin at the rate of 440 kg/ha). While this method is useful in research plots, it is prohibitively expensive for use as a commercial control method.

The fungicide metalaxyl [N-(2,6-dimethylphenyl)-N-(methoxyacetyl)alanine methyl ether] is currently registered for control of Pythium spp.; however this treatment has only limited usefulness because some of the naturally occurring Pythium strains are tolerant to this fungicide. Additionally, for a fungicide to be effective against Pythium, it must be absorbed by the plant and translocated downward systemically in the plant; presently all systemic fungicides available commercially for Pythium control move only in an upward direction in the plant and thus are only minimally effective. Currently, no Pythium resistant varieties of small grains are known.

While use of antagonistic microorganisms as seed or soil treatments for biological control of some root or seedling pathogens has been reported for a variety of plants, no bacterial strain has been previously found which would control Pythium spp. on small grain crops; additionally, no procedure for the selection of bacteria which suppress Pythium in small grains has been reported. Because the physiological characteristics required for a bacterial strain to control disease are very specific as to (1) the disease which is to be controlled; (2) the plant which is effected; (3) the mode of action of the disease control; (4) the activity of the microorganism; (5) the ecological niche of the pathogen and control organism; (6) cultural practices favorable to the disease, and (7) soil and climatic conditions favorable to disease, information about biological treatments for control of other fungal diseases on small grains or control species of Pythium on other plants cannot be used to predict strains of microorganisms which would control Pythium spp. on small grains under field conditions or predict criteria for selecting such strains.

SUMMARY OF THE INVENTION

We have discovered a novel method for screening bacteria to select those strains which will suppress (reduce the incidence or severity of) disease in small grain crops such as wheat, oats, barley, rye, triticale, and related crops caused by the pathogen complex Pythium spp. When used as a seed or furrow treatment, the novel bacteria obtained by our method have the ability to suppress Pythium spp. under field conditions.

We have also discovered four novel strains of fluorescent Pseudomonas which are effective in suppressing Pythium spp. in field grown wheat.

Our screening method comprises:

1. Isolating strains of bacteria having potential for suppressing Pythium spp. from the rhizoplane (root surface) or rhizosphere (soil immediately surrounding the roots) or both rhizoplane and rhizosphere of small grain crops grown in soil containing Pythium spp. in a concentration of 500–1,000 spores/gram of soil.

2. Screening the bacterial strains selected in step 1 in the greenhouse as follows: growing the small grain crop to be protected in the greenhouse in the presence of the bacterial strain selected in step 1 in a concentration of about $10^6$–$10^8$ bacteria/crop seed in soil containing Pythium spp. in a concentration of about 500–1,000 spores/gram of soil; growing control plants as above but without the addition of the bacteria; and selecting as greenhouse-suppressive bacteria those strains which cause the treated plants to exhibit greater overall height or longer first true leaves.

3. Screening the bacterial strains selected in step 2 in the field as follows: growing in the field the small grain crop to be protected in the presence of the bacterial strain selected in step 2 in a concentration of $10^6$–$10^8$ bacteria/crop seed or $10^{11}$–$10^{12}$ bacteria/3-meter row (furrow treatment) in soil containing Pythium spp. in a concentration of 500–1,000 spores/gram of soil; growing control plants as above but without the addition of the bacteria; and selecting as field-suppressive bacteria those strains which cause the treated plants to exhibit greater height, greater stand, greater yield, or more heads.

The bacterial strains selected by the above process have the ability to control Pythium spp., i.e., reduce incidence or severity of the disease, under field conditions when used as a soil or furrow treatment.

In accordance with this discovery, it is an object of the invention to provide a means for screening bacteria to select those strains which suppress disease-causing Pythium spp. in small grain crops under field conditions.

It is also an object of the invention to provide a method for biologically controlling Pythium spp. in small grain crops using the so-selected bacterial strains.

Another object of the invention is the provision of novel strains of *Pseudomonas fluorescens* and *Pseudomonas putida* which suppress Pythium spp. on field grown wheat.

Other objects and advantages of the invention will become apparent from the ensuing description.

DESCRIPTION OF THE PREFERRED EMBODIMENTS

The screening method comprises:

Step 1. Isolation of Strains of Potentially Suppressive Bacteria

To biologically control root disease caused by Pythium spp., a bacterial strain must have the ability to colonize the root system of the small grain crop to be protected. Such bacteria are selected by isolating strains from the rhizoplane (root surface) or rhizosphere (soil immediately surrounding the roots) or both rhizoplane and rhizosphere of small grain crops grown in soil containing naturally occurring or added Pythium spp. Although strains from the soil from the rhizoplane or rhizosphere of one small grain (e.g., wheat) may be isolated in this step for potential use to control Pythium on another crop (e.g., rye), it is preferred that the bacterial strain be isolated from the variety of small grain to be protected as it is likely to best colonize this variety.

It is within the compass of the invention to isolate any type of bacteria having the potential to suppress Pythium, however fluorescent pseudomonads are the bacteria of choice because (1) they can be easily isolated, cultured and identified; (2) they normally inhabit rhizosphere soil; (3) they are nutritionally versatile, being able to utilize a large number of organic substrates, including, root exudates; (4) they have a fast growth rate relative to other bacteria in the rhizosphere; (5) some strains produce antibiotics and siderophores that can inhibit phytopathogenic bacteria and fungi in vitro; and (6) they can be successfully introduced into the root system of small grains crops and become established in the rhizosphere and rhizoplane.

Because Pythium spp. are found in most, if not all, agricultural soils, the small grain crop can be grown in soil containing only the naturally occurring mixture of species of Pythium. However, if desired, Pythium spp. may be added to the soil in which the crop is grown. In either case, the concentration of Pythium spp. in the soil should be 500–1,000 spores/gram of soil.

The bacteria are collected and isolated by standard procedures. For example, bacteria of the genus Pseudomonas can be isolated by macerating the roots with adhering soil in 0.01M phosphate buffer using a mortar and pestle. Serial dilutions of the homogenate are prepared and spread-plated on various media to obtain single colonies. Then, the pseudomonads are plated on a selective media such as King's Medium B (KMB) or on KMB supplemented with novobiocin, penicillin, and cycloheximide (NPC). Fluorescent pseudomonads can be detected by viewing the plates under UV light and observing fluorescence.

Individual strains (colonies) of bacteria are individually streaked onto a suitable media and selected and restreaked until the strain is pure and stable. Each individual strain is maintained so as to keep it stable such as by storing in 40% glycerol at $-10°$ C. or lyophilizing and storing at $-10°$ C.

Step 2. Screening of the Bacterial Strains in the Greenhouse

Bacterial strains isolated in the previous step are screened to select those strains which, at a particular concentration, suppress Pythium spp. in small grain crops under greenhouse conditions.

In this test, sterilized seeds of the small grain variety to be protected are coated with the candidate strains at a concentration of $10^6$–$10^8$ bacteria/seed. This may be conveniently done by either of the following ways: (1) suspending the bacteria in water containing 0.1M $MgSO_4$, adjusting the population to $10^8$–$10^9$ colony forming units (CFU), and soaking the seeds in the suspension for 30 minutes or (2) adding the bacteria to a suspension containing 0.5 to 2 percent of a suspending agent such as methylcellulose in water (eight plates of bacteria per 50 ml methylcellulose solution per 100 g seed) and drying the seeds overnight in an air stream.

The seeds are grown in soil containing naturally occurring or added Pythium spp. In either case, the concentration of Pythium spp. should be 500–1,000 spores/gram of soil. A 15-cm tube (2.5 cm diameter) has been found to be a convenient size for the greenhouse test. The tube is filled about three-quarters full with soil, followed by 1–2 bacterial treated seeds and a 2-cm thick topping of soil and vermiculate mixed 1:1 (v/v). Another convenient container for greenhouse testing is a 500-ml cup. The cup is filled with about 400 g soil, followed by up to about 5 seeds and then a covering of soil.

After about 3 to 4 weeks, the seedlings are pulled up and the total height or the length of the first true leaf are determined and compared to controls which are grown identical to treated plants except without bacterial treatment.

Bacterial strains which cause treated seedlings to average at least 1 cm taller or first true leaves to average at least 0.5 cm longer compared to untreated seedlings are considered suppressive to Pythium spp. in this test. To have statistical significance, a minimum of three tubes or three cups per treatment should be used.

Step 3. Screening the Bacterial Strains in the Field

Bacterial strains selected in the previous step are tested for suppressiveness under field conditions as follows: Field plots containing naturally occurring or added Pythium spp. to provide a concentration of 500–1,000 spores/gram of soil are planted with seeds of the small grain crop of the variety to be protected in the presence of the test bacterial strain. The bacterial treatment comprises either treated seeds having a concentration of about $10^6$–$10^8$ bacteria/seed or a furrow treatment have a concentration of about $10^{11}$–$10^{12}$ bacteria/3-meter row.

The plots should be laid out in a manner suitable for statistical evaluation. It is preferred that the control plot (plot identical to the test plot but without bacterial treatment) be within close proximity to the comparable treatment plot rather than distributed randomly so that the treatment and control plots have similar soil conditions, soil moisture, etc. The preferred treatment plot size is three or four 3-meter rows with a control plot within about three meters of the treatment plot.

To assess the effect of the bacterial treatment in the suppression of Pythium spp. in the field, measurements such as plant stand, plant height, number of heads, or grain yield are taken at intervals throughout the growing season and at maturity or a minimum of at least four weeks after planting. In order for a bacterial strain to be considered suppressive to Pythium spp. in the field, the plants treated with the bacterial strain must average at least 1 cm taller, 5 percent more heads, five percent greater stand, or five percent greater yield. The preferred evaluation procedure is the head count or yield determination.

To minimize the number of strains to be screened in the greenhouse, it is useful to screen the bacterial strains isolated in step 1 using an in vitro step prior to testing in the greenhouse. In the in vitro test, the strain is spotted on the edge of a suitable agar plate (petri dish) and an 8-mm diameter plug of a Pythium spp. isolate is placed in the center of the dish. The plate is maintained at a suitable time and temperature to allow the bacteria to grow and zones of inhibition of the strains are measured. Strains which show zones of inhibition of at least 1 mm are selected as potentially suppressive bacteria in this test. Where pseudomonads are tested in the in vitro screening test, suitable agar media include King's Medium B and Potato Dextrose Agar.

Method Of Application Of Pythium-suppressive Bacteria for Field Control in a Commercial Setting To control Pythium spp. in small grain crops in a commercial field, either the seed or the seed furrow is treated with the suppressive bacterial strain. Where control is with treated seeds, the seeds are coated with $10^6$–$10^8$ bacterial/seed, and preferably $10^8$ bacteria/seed using a sticking agent such as methycellulose as described above. The seeds are dried and clumps of seeds are broken up so that they can be sown using commercial seeder such as a grain drill. Where control is with a furrow treatment, the concentration is $10^{11}$–$10^{12}$ bacteria/3-meter row. One convenient way to treat furrows is to prepare a suspension containing $1 \times 10^9$–$5 \times 10^{10}$ bacteria/ml and add about 1 liter of the bacterial suspension to each 3-meter long row.

EXAMPLES

The method of the invention is next demonstrated by the following illustrative examples.

EXAMPLE 1

Isolation of Pseudomonas Strains from Wheat Roots

Winter wheat (cv. Daws) plants grown in a field in Washington State where wheat is normally grown and containing naturally occurring Pythium spp. in a concentration of about 600 spores/gram of soil were uprooted and the roots shaken to remove all but the rhizosphere (closely adhering) soil. The roots and adhering soil were macerated in a mortar and pestle with 0.01M phosphate buffer (pH 7.2). Aliquots of 0.1 ml of a dilution series of $1 \times 10^{-1}$, $1 \times 10^{-2}$, $1 \times 10^{-3}$ and $\times 1 \times 10^{-4}$ were spread-plated onto King's Medium B (KMB) (Proteose peptone, 20 g; glycerol, 10 ml; $K_2HPO_4$, 1.5 g; $MgSO_4$, 1.5 g; agar, 15 g; $H_2O$, 1000 ml) and KMB supplemented with novobiocin, penicillin and cycloheximide and grown at 25° C. for four days. Fluorescent pseudomonads were detected by viewing the plates under UV light.

Pure isolates of the individual strains were obtained by subculturing a strain on Nutrient Broth Yeast Extract Medium (NBY) (Bacto-nutrient broth, 8 g; Bacto-yeast extract, 2 g; $K_2HPO_4$, 2 g; $KH_2PO_4$, 0.5 g; $MgSO_4.7H_2O$, 0.25 g; glucose, 5 g; agar, 15 g; $H_2O$, 1000 ml) to obtain a pure culture. Each isolate was stored in a aqueous solution of 40% glycerol at −10° C. or lyophilized and stored at −10° C.

EXAMPLE 2

Screening of Bacterial Strains in Vitro

Individual bacterial strains obtained by the procedure outlined in Example 1 were screened for the ability to suppress Pythium spp. in vitro as follows: Isolates were spotted at the edges of agar plates (petri dishes) of King's Medium B and potato dextrose agar (PDA). A 8-mm diameter plug of a Pythium isolate obtained from the edge of a culture growing on POA was placed in the center of the plate and cultured at 24° C. for three days. Zones of inhibition were measured and those showing clear zones greater than 1 mm were selected as suppressive to Pythium spp. in this test. Of 5,000 strains tested in vitro, only 350 were determined to be inhibitory to Pythium spp.

EXAMPLE 3

Screening of Bacterial Strains in the Greenhouse

Pseudomonas strains that were suppressive to Pythium spp. in vitro were screened in the greenhouse by growing bacteria treated wheat seeds in Puget silt loam containing naturally occurring Pythium spp. and comparing the treated wheat with control wheat plants grown without bacterial treatment.

a. Bacterial seed treatment. Wheat seeds (cv. Fielder) were first surface sterilized by immersing the seeds in a 20% bleach (5.25% sodium hypochlorite) for three minutes, followed by several rinses with sterile, distilled water, and drying overnight under an air stream.

Each bacterial test strain was cultured by flooding a petri plate of KMB with 3 ml of a turbid suspension of the test strain and incubating for 2 days at room temperature.

Bacteria were applied to the seed to provide a concentration of $10^6$–$10^8$ bacteria/seed by either of the two following methods. In the first method, bacteria were scraped from the plates with a glass rod into a suspension of 1.0% methycellulose, and thoroughly mixed with wheat seed (eight plates of bacteria per 50 ml methylcellulose solution per 100 g seed). Coated seeds were distributed as a thin layer into petri dishes, dried overnight under an airstream, and separated prior planting.

In the second method, bacteria were suspended in a $0.1M$ $MgSO_4$ aqueous solution and the concentration adjusted to $10^9$ CFU/ml. Wheat seeds were soaked in the suspension for 30 minutes.

b. Greenhouse screening procedure. Bacterial treated wheat seeds prepared as described as above and control (untreated) wheat seeds were grown in Puget silt loam containing natural inoculum of Pythium spp. in a concentration of about 600 spores/gram of soil as follows: Conical-shaped, free draining tubes (15-cm long, 2.5-cm diameter), supported in a hanging position, 200 tubes/rack, were filled three quarters full with soil which had been air dried and screened to pass thru a 1 mm mesh, then two seeds (either test or control) were placed on the soil and covered with a 2-cm thick topping of soil and verimiculite mixed 1:1 (v/v). Prior to planting, the bottoms of the tubes were immersed in water to allow wetting of the soil by capillary action. After planting, the tubes were incubated in a growth chamber at 15°–18° C. for three weeks using a dark/light cycle of 12 hours. The tubes were watered once with 10 ml of ⅓ strength Hoagland's solution (macro elements only) 10 days after planting and then with 5 ml of water every four days. The racks were covered with plastic until the shoots emerged. Ten tubes were used for each test strain and control.

After three weeks, the plants were harvested, washed with water, and measured from the base of the stem to the top of the largest leaf or from the stem to the tip of the first true leaf. In order for the bacterial strain to be considered suppressive to Pythium spp., the seedlings treated with the bacteria must have averaged at least 1 cm taller or have a first true leaf 0.5 cm longer than comparable untreated but diseased seedlings. Of 400 bacterial strains tested in the greenhouse test, about 30% were determined to be suppressive according to the above criteria. The test results for 19 strains which passed the greenhouse screening test are given in Table 1.

TABLE 1

| Bacterial Strain | Plant Height (cm) | Difference (cm) |
| --- | --- | --- |
| Qa72 (NRRL B-15815) | 22.0 | 10.5 |
| Qy6 | 23.9 | 12.4 |
| Qz14 | 20.0 | 8.5 |
| Control | 11.5 | |
| Ry5 (NRRL B-15819) | 17.4 | 5.9 |
| Ry7 | 19.2 | 7.7 |
| Control | 11.5 | |
| Rz3 | 22.9 | 7.0 |
| Rz8 (NRRL B-15818) | 21.9 | 6.0 |
| Qz3 | 21.4 | 5.5 |
| Qz15 | 21.8 | 5.9 |
| Control | 15.9 | |
| Mz4 | 14.8 | 5.7 |
| Mz7 | 15.5 | 6.4 |
| Mz8 | 17.9 | 8.8 |
| Mz12 | 15.6 | 6.5 |
| Qz28 | 16.3 | 7.2 |
| Qz29 | 15.9 | 6.8 |
| Qz31 | 16.6 | 7.5 |
| Control | 9.1 | |
| Mz29 | 22.1 | 7.1 |
| Mz33 | 20.8 | 5.8 |
| Qz30 (NRRL B-15816) | 20.9 | 5.9 |
| Control | 15.0 | |

EXAMPLE 4

To show that the increase in plant height was due to the suppression of Pythium spp. by the test bacterial strain, wheat seeds treated with strain Qa72 (NRRL B-15815) were grown in Pythium-containing soil with and without the Pythium-specific fungicide, metalaxyl; and seeds with and without methylcellulose were grown in the soil with and without metalaxyl.

Strain Qa72 was isolated and propagated according to Example 1. The pure strain was grown on King's Medium B for 48 hours, scraped into a 0.5% suspension of methylcellulose, mixed with Fielder wheat seed, and dried to provide a concentration of $10^8$ bacteria/seed. Wheat seed was also treated with only 0.5% methylcellulose. Untreated wheat seed was used as a control.

The test procedure was as follows: 400 g of Puget silt loam containing naturally occurring Pythium spp. in a concentration of about 600 spores/gram of soil were placed in pots (500-ml paper drinking cups) and watered with 100 ml of diluted (1:3, v/v) Hoagland's solution with or without 0.0125 ml of metalaxyl (Ciba-Geigy, Greensboro, N.C. 48898) at 2.5 mg/ml active ingredient. Five seeds were sown in each pot and then covered with 50 g of soil. The pots were held in the greenhouse at 15°–18° C. for four weeks using a light/dark cycle of 12 hours. The pots were covered with plastic until the seeds germinated and then watered each week with 25 ml of water. Five pots were used for each test and control.

As can be seen from the results which are presented in Table 2, strain Qa72 significantly increased plant growth as compared to untreated wheat and this improvement was due to the suppression of Pythium spp. since the growth response was duplicated by the addition of the Pythium specific fungicide.

TABLE 2

| Treatment | Plant Height (cm)[a] |
| --- | --- |
| Qa72 (NRRL B-15815) | 22.7 |
| Qa72 + metalaxyl | 24.0 |
| Methylcellulose + metalaxyl | 23.2 |
| Untreated + metalaxyl | 25.4 |
| Methylcellulose | 14.6 |
| Untreated | 12.4 |

[a]The least significant difference at P = 0.05 is 5.6.

EXAMPLE 5

Field Screening Test

Strains Qa72 (NRRL B-15815), Ry5 (NRRL B-15819), Rz8 (NRRL B-15818), and Qz30 (NRRL B-15816), which passed the greenhouse test, were field tested in Pullman, Wash. during the 1982–1983 growing season. Treatments consisted of plots of three 3-meter long rows with a row spacing of 41 cm. Each treatment row was planted next to three rows of untreated wheat. The bacterial strains were isolated and propagated as described in Example 1. Bacteria in a 1.5% suspension of methycellulose were applied to Daws wheat seed to provide $1 \times 10^8$ bacteria/seed. Control seeds received no bacterial treatment or methylcellulose. The soil contained naturally occurring Pythium spp. in a concentration of about 600 spores per gram of soil.

Seed furrows were opened to about a 10-cm depth with a cultivator with a single V-shovel. Seed was sown at a rate of 7.5 g seed/3-meter row. The following measurements were made: The number of plants/3-meter row were counted 167 days after planting; plant height from the soil surface to the tip of the longest leaf was measured 223 days after planting; the number of heads/3-meter row was counted 244 days after planting; and the yield (grain weight/3-m row) was measured at maturity. All measurements were made on two rows per treatment replication. In order for the bacterial strain to be considered suppressive to Pythium spp. in the field test, the treated plants must have 5% greater stand (number of plants that come up), 1.0 cm greater height, 5% more heads, or 5% greater yield than the controls. As can be seen from the data in Table 3, all four strains passed the field test. Compared to the control wheat, strains Rz8 and Qz30 significantly increased the number of heads, strain Ry5 increased the plant stand and plant height, and strain Qa72 improved plant performance based on all four parameters.

TABLE 3

| Bacterial strains | No. of plants | Plant height (cm) | Heads | Yield (g) |
| --- | --- | --- | --- | --- |
| Qa72 | 94 a[a] | 83.9 a[a] | 461 a[a] | 716 a[a] |
| Control | 53 b | 80.7 b | 381 b | 567 b |
| Rz8 | 72 a | 83.3 a | 443 a | 665 a |
| Control | 60 a | 81.5 a | 377 b | 602 a |
| Ry5 | 82 a | 86.2 a | 491 a | 720 a |
| Control | 53 b | 84.0 b | 407 a | 599 a |
| Qz30 | 70 a | 83.7 a | 487 a | 659 a |
| Control | 63 a | 83.3 a | 427 b | 647 a |

[a]All data is expressed on the basis of a single 3-meter row. Means followed by the same letter are not signficantly different (P = 0.05).

EXAMPLE 6

Strains Qa72 (NRRL B-15815), Rz8 (NRRL B-15818), Ry5 (NRRL-15819), and Qz30 (NRRL B-15816) passed the screen test outlined above and have the ability to suppress Pythium spp. in wheat when used as a seed or soil treatment. These strains have been deposited in the Agricultural Research Culture Collection (NRRL) in Peoria, Ill. 61604 and have been assigned the accession numbers noted.

Strains Qa72, Rz8, and Qz30 are *Pseudomonas fluorescens* and strain Ry5 is *Pseudomonas putida*. The characteristics of these Pythium-suppressive pseudomonads are given in Table 4.

TABLE 4

|  | Qa72 (B-15815) | Qz30 (B-15816) | Rz8 (B-15818) | Ry5 (B-15819) |
|---|---|---|---|---|
| Fluorescent Pigments | + | + | + | + |
| Pyocyanine | − | − | − | − |
| Carotenoids | − | − | − | − |
| Growth at 41° C. | − | − | − | − |
| Levan formation from sucrose | + | + | + | − |
| Arginine dihydrolase | + | + | + | + |
| Oxidase reaction | + | + | + | + |
| Dentrification | − | − | + | − |
| Hydrolysis of: | | | | |
| Gelatin | + | + | + | − |
| Starch | − | − | − | − |
| Carbon sources for growth: | | | | |
| Glucose | + | + | + | + |
| 2-Ketogluconate | + | + | + | + |
| B-Alanine | + | + | + | + |
| DL-Arginine | + | + | + | + |
| L-Arabinose | + | + | +− | − |
| Sucrose | + | + | + | +− |
| Sorbitol | − | − | + | − |
| Propylene glycol | − | − | + | − |
| Ethanol | − | − | + | − |
| Mannitol | + | + | + | +− |
| Cellobiose | − | − | − | − |
| D-galactose | + | + | +− | +− |
| L-Ornithine | + | + | − | + |
| Glycine | − | − | − | + |
| Benzylamine | − | − | − | − |
| DL-Tryptophane | − | − | − | + |
| D-Alanine | + | + | + | + |

It is understood that the foregoing detailed description is given merely by way of illustration and that modification and variations may be made therein without departing from the spirit and scope of the invention.

Having thus described our invention, we claim:

1. A method for screening bacteria for strains which will suppress Pythium spp. in field grown small grain crops, which comprises:
    (a) isolating a strain of bacteria from the rhizoplane, rhizosphere, or both rhizoplane and rhizosphere of small grain crops grown in soil containing Pythium spp. in a concentration of 500–1,000 spores/gram of soil;
    (b) screening said strain isolated in step (a) for suppression of Pythium spp. in the greehouse as follows:
        (1) growing the small grain crop of the variety to be protected in the greenhouse in the presence of said strain selected in step (a) in a concentration of $10^6$–$10^8$ bacteria/crop seed in soil containing Pythium spp. in a concentration of about 500–1,000 spores/gram of soil;
        (2) growing the small grain crop of the variety to be protected as in step (b)(1) without the addition of said strain; and
        (3) selecting a strain which caused the plants of (b)(1) to average at least 1.0 cm taller or to have first true leaves which averaged at least 0.5 cm longer than plants grown in (b)(2);
    (c) screening said strain selected in step (b)(3) for suppression of Pythium spp. in the field as follows:
        (1) growing the small grain crop of the variety to be protected in the field in the presence of said strain selected in step (b)(3) in a concentration of about $10^6$–$10^8$ bacteria/crop seed or $10^{11}$–$10^{12}$ bacteria/3-meter furrow in soil containing Pythium spp. in a concentration of 500–1,000 spores/gram of soil;
        (2) growing the small grain crop of the variety to be protected as in step (c)(1) without the addition of said strain; and
        (3) selecting a strain which caused the plants of (c)(1) to average at least 1 cm taller, 5 percent more heads, 5 percent greater stand, or 5 percent greater yield than plants grown in (c)(2).

2. The method of claim 1, further comprising:
    (d) applying said strain of bacteria selected in step (c)(3) to seeds of the small grain crop of the variety to be protected in a concentration of about $10^6$–$10^8$ bacteria/seed.

3. The method of claim 1, further comprising:
    (d) applying said strain of bacteria selected in step (c)(3) to the seed furrow of the small grain crop of the variety to be protected in a concentration of about $10^{11}$–$10^{12}$ bacteria/3-meter furrow.

4. The method of claim 3 wherein said strain of bacteria which is applied in step (d) is in suspension.

5. The method of claim 1, further comprising screening said strain isolated in step (a) in vitro prior to screening in the greenhouse as follows: spotting said strain on an agar plate, placing an 8-mm diameter plug of a Pythium spp. isolate in the center of the plate, growing said strain, and selecting a strain which shows a zone of inhibition of at least 1 mm.

6. The method of claim 1 wherein the small grain crop to be protected is wheat.

7. A product comprising small grain crop seed coated with a biologically pure culture of bacteria which suppresses disease caused by Pythium spp. in small grain crops under field conditions as determined by passing the screening test of claim 1, the concentration of said bacteria being $10^6$–$10^8$ bacteria/seed.

8. A method of suppressing disease caused by Pythium spp. in small grain crops in the field, which comprises growing the small grain crop of the variety to be protected in the presence of a biologically pure culture of a bacteria which suppresses disease caused by Pythium spp. under field conditions as determined by passing the screen test of claim 1, the concentration of said bacteria being $10^6$–$10^8$ bacteria/seed or $10^{11}$–$10^{12}$ bacteria/3-meter furrow.

9. The method of claim 8 wherein said biologically pure culture of bacteria comprises a strain of Pseudomonas.

10. The method of claim 9 wherein said strain of Pseudomonas bacteria is elected from the group consisting of *Pseudomonas fluorescens* and *Pseudomonas putida*.

11. The method of claim 10 wherein said strain of Pseudomonas bacteria is selected from the group consisting of NRRL B-15815, NRRL B-15816, NRRL B-15818, and NRRL B-15819.

12. A biologically pure culture of bacteria which suppresses disease caused by Pythium spp. in small grain crops under field conditions as determined by passing the screen test of claim 1.

13. The biologically pure culture of claim 12 wherein said culture of bacteria comprises a strain of Pseudomonas.

14. The biologically pure culture of claim 13 wherein said strain of Pseudomonas is selected from the group consisting of *Pseudomonas fluorescens*, and *Pseudomonas putida*.

15. The bioligically pure culture of claim 14 wherein said strain of Pseudomonas is selected from the group consisting of NRRL B-15815, NRRL B-15816, NRRL B-15818, and NRRL B-15819.

* * * * *